United States Patent
Singer et al.

(10) Patent No.: US 9,970,916 B2
(45) Date of Patent: May 15, 2018

(54) WELLHEAD WATER QUALITY DETECTOR

(71) Applicant: WellIntel, Inc., Shorewood, WI (US)

(72) Inventors: Marian J. Singer, Whitefish Bay, WI (US); Nicholas D. Hayes, Shorewood, WI (US); Joseph H. Fillingham, Milwaukee, WI (US)

(73) Assignee: WellIntel, Inc., Shorewood, WI (US)

( * ) Notice: Subject to any disclaimer, the term of this patent is extended or adjusted under 35 U.S.C. 154(b) by 474 days.

(21) Appl. No.: 14/812,845

(22) Filed: Jul. 29, 2015

(65) Prior Publication Data

US 2016/0033462 A1 Feb. 4, 2016

Related U.S. Application Data (60) Provisional application No. 62/030,601, filed on Jul. 29, 2014.

(51) Int. Cl.
*G01N 33/00* (2006.01)
*G01N 33/18* (2006.01)
*E03B 3/15* (2006.01)

(52) U.S. Cl.
CPC ............ *G01N 33/0047* (2013.01); *E03B 3/15* (2013.01); *G01N 33/18* (2013.01)

(58) Field of Classification Search
CPC ........................... G01N 33/0047; G01N 33/18
See application file for complete search history.

(56) References Cited

U.S. PATENT DOCUMENTS

| 4,586,033 | A * | 4/1986 | Andrejasich | G01N 27/045 340/521 |
| 8,215,164 | B1 * | 7/2012 | Hussain | E21B 43/14 73/152.33 |
| 9,784,093 | B2 * | 10/2017 | Bourgeois | G01F 23/24 |
| 2003/0080604 | A1 * | 5/2003 | Vinegar | E21B 43/243 299/14 |
| 2014/0009302 | A1 * | 1/2014 | Singer | E21B 47/042 340/853.1 |

FOREIGN PATENT DOCUMENTS

WO    WO 2014005099 A1 *    1/2014    ........... E21B 47/042

OTHER PUBLICATIONS

Matheson et al., "How Well Do You Know Your Water Well?", 2012, pp. 1-34.*
Kiernan et al., "Monitoring of Gas Emissions at Landfill Sites Using Autonomous Gas Sensors", 2010, Environmental Protection Agency,2005-AIC-MS-43-M4, pp. 1-35.*

* cited by examiner

*Primary Examiner* — Mischita Henson
(74) *Attorney, Agent, or Firm* — Andrew C. Landsman; Godfrey & Kahn, S.C.

(57) ABSTRACT

A module gathers information about water quality indicators in the air above water in a water well and in the ambient air outside the water well. The module sends the information to a database. A detector tracks the substances present inside and outside the well and how it changes over time.

21 Claims, 5 Drawing Sheets

WELLHEAD WATER QUALITY DETECTOR

CROSS-REFERENCE TO RELATED APPLICATION

This application is based on and claims priority to U.S. Provisional Patent Application No. 62/030,601 filed on Jul. 29, 2014, which is incorporated herein by reference in its entirety for all purposes.

FIELD OF THE INVENTION

The present invention relates generally to the field of well water information and devices and methods of retrieving and recording said information. More particularly, the present invention relates to devices and methods of continuously monitoring water quality indicators present in the air in and around a well.

BACKGROUND

Many residential homeowners rely on the use of private wells to supply water to their home. Likewise, many farmers rely on the use of wells to supply water to irrigate crops or to keep animals hydrated. Private water wells are a common feature in areas where municipal or city water services are unavailable or where surface supplies are not sufficient or accessible. Water wells are commonly used to source groundwater where naturally occurring groundwater exists in spaces between rocks and/or sand. The wells themselves are bore holes either drilled or pressed into or through the ground into which casing pipes, screens, pumps and other water plumbing are installed. Groundwater seeps through openings in the casing pipe called screens. Water can be pumped via these wells, either with an above ground vacuum pump or, where the water is deeper than 30 feet, with a submersed pump that creates upward pressure to move the water to the surface.

A conventional well typically includes a borehole from the surface to a required depth to reach the groundwater. A casing pipe is inserted into the borehole and grout is used to seal the space between the casing pipe and the earth. A pump (either submersed or above the groundwater surface, depending on depth) is attached to the water pipe for transportation of water from the well to the point of use. The well is capped at the wellhead on the ground surface with a well cap. Typically, information which may include a service contractor's phone number and a date of service may be recorded on the well cap.

Water well construction and sometimes site selection or location advisement is done by a well driller, who takes care to design the well to meet the needs of those who will use the water. The well driller, in the process of planning and drilling, will determine where there is ample groundwater, and will size the length and diameter of the well and casing pipe and the capacity and location of the pump accordingly. The well driller will take special care to know the top elevation and the productivity of the groundwater table. Elevation is often found by measuring down from the wellhead (top of the well) to the water surface. Productivity of the well is inferred by measuring the elevation of the water and time it takes to return to a resting level after a pumping event has removed water from the well. Together with elevation and productivity, the final pump selection is made and construction can be completed.

In addition to locating a well in a correct location and at the correct depth to maximize the groundwater productivity of the well, the well also needs to produce groundwater of acceptable quality for use by the well owner. Water quality is important to the well owner because only water of sufficiently high quality may be used safely for human consumption and other domestic and agricultural uses. A well that is contaminated by either natural or human impacts may cause water from the well to be unacceptable and not usable to the well owner. The United States Environmental Protection Agency (EPA) sets maximum contaminant levels (MCLs) for many natural and human introduced contaminants in the environment which serve as human health benchmarks for drinking water. The well owner may also establish specific quality standards based on the use of the well water including human consumption, animal consumption, crop watering, manufacturing and processing requirements, and the like. If the water from the well does not meet the EPA's or the well owner's water quality standards, the well owner may need to remediate or abandon the well. These actions are often expensive and could limit the amount of water the well owner is able to draw from the land.

When commissioning or repairing a well, a well driller may also perform an initial water quality indicator test of the well to determine whether the well location will produce acceptable water quality. In the event a certain water quality indicator, or concentration of a chemical is detected, the well driller may notify the well owner to determine if the well water is acceptable to the well owner.

There are many water quality indicators which the well owner may wish to detect and monitor, especially substances which are harmful to the well owner's health and property. Some non-limiting examples of these substances are volatile organic compounds (VOC), radon, radiation, natural gas, oil, and the like.

One method used to measure the water quality of the well water is by taking physical samples of the water. Such water samples can be taken from the well by removing the wellhead cap and using equipment to take water samples from the well. Removal of a well cap and direct sampling of well water requires specialized training and certification due to the possibility of groundwater contamination and therefore incurs a high cost to the well owner. Alternately, water samples can be taken from the water pumped from the well. Testing for certain substances from water samples pumped from the well can be disadvantageous due to changes in water properties during pumping and transport of the water. Both of these two processes require samples to be sent to an offsite laboratory which incurs high costs and substantial wait times for information. Submersible devices are available that can monitor water quality indicators in well water, log these data through time, and provide accurate information at a high temporal frequency. These devices and methods are generally extremely costly and often require specialized training to calibrate the submerged sensors, as well as to download and interpret data. In addition, these devices require manual data retrieval which does not provide the ability to take immediate action due to a rapid change in water quality and can lead to the loss of data if the device fails without the owner's knowledge.

There are many water quality indicators and contaminants which the well owner may wish to detect and monitor, especially substances that are harmful to the well owner's health and property. Examples of water quality indicators are the concentration of total dissolved solids, chloride, dissolved oxygen, trace metals such as iron and manganese, the pH level, the specific conductance, and turbidity. Substances that are of interest as they impact human health are nitrate, sulfate, volatile organic compounds (VOCs), radon and other radionuclides, arsenic, natural gas, pesticides microbial contaminants, and the like.

Another way to measure water quality indicators is by measuring water quality indicators in the air in the well above the groundwater level. Air is present within the well between the groundwater level and the well cap. Certain volatile water quality indicators and contaminants such as VOCs, radon, natural gas, certain pesticides, and the like, are present within this air due to the exchanges of substances across the air-water interface. These volatile substances may accumulate in the wellhead air space due to the minimal exchange of air between the wellhead space and the outside of the well, ambient air. The transfer of volatile compounds across the air-water interface is controlled by the solubility of the dissolved gas in water, which is often dependent on water temperature, molecular diffusion at the air-water interface, and turbulent diffusion in both the air and water columns. Accordingly, the detection of volatile water quality indicators in the well air, and tracking their change in time, provides an indication of their presence in the well water and provide important information to the well owner of well water contamination and the need for further testing.

As such, there is a need for a device that continuously monitors water quality indicators present in and around a well. What is also needed is a way to monitor the water quality indicators present in a well without repeatedly removing the well cap and subjecting the well owner to the expense of manual well water sampling, laboratory analysis requiring long wait times, and the purchase of expensive equipment which requires specialized training to operate and interpret data. Further, what is needed is a way to retrofit existing wells with a device that monitors water quality indicators in a well without repeatedly removing the well cap or physically removing water from the well for analysis unless it is necessary. Heretofore, these requirements have not been fully met without incurring various disadvantages.

SUMMARY

The present invention relates to a wellhead water quality detector that allows continuous monitoring and detection of water quality indicators present at a wellhead. The wellhead water quality detector includes two sensors, a sensing circuit, an environmental sensor for calibration, a clock, a data logger, and power and communication circuits. The water quality sensors detect water quality indicators in the air inside the well and the air outside the well. The wellhead water quality detector also communicates the water quality data to a globally accessible network.

In an alternative embodiment, a wellhead water quality detector includes air tubes to a sensor and to open air outside of the well. These air tubes are added to the sensors, sensing circuit, environmental sensors for calibration, clock, data logger, and power and communication circuits. The air tubes guide air to be detected to and from the sensors.

An alternative embodiment of the invention is a wellhead water quality detector having a simple, solar-powered sensor and communication module that gathers information about a water quality indicator in a borehole-style water well and sends the information to a database that a homeowner can access via a computer, handheld device, or smart phone. The wellhead water quality detector in the well can be programmed to send alerts to interested parties when user-predetermined thresholds are reached. The wellhead water quality detector and a website enable a well owner to use water mindfully, and can help prevent costly remediation, contamination, or other emergencies.

The wellhead water quality detector can preferably be attached to the exposed wellhead or an existing previously-installed sensor system by a handy homeowner using a few common tools. In some applications, only a replaceable battery is required to power the sensor. And in others, power can be harvested from existing power wiring, without connections, using a current transducer and a power monitoring circuit. And in others, a photovoltaic cell affixed to the wellhead substance detector or, optionally, on a flexible wand to raise the solar cell, charges and recharges a battery which powers all functions. The wellhead water quality detector is installed just inside the existing well cap, through vent holes that may be in the existing well cap, or within a new, replacement well. The data it collects is compiled in memory and sent to a database, where it is stored and analyzed.

It will be understood by those skilled in the art that one or more aspects of this invention can meet certain objectives, while one or more other aspects can lead to certain other objectives. Other objects, features, benefits and advantages of the present invention will be apparent in this summary and descriptions of the disclosed embodiment, and will be readily apparent to those skilled in the art. Such objects, features, benefits and advantages will be apparent from the above as taken in conjunction with the accompanying figures and all reasonable inferences to be drawn therefrom.

DETAILED DESCRIPTION

Figure 1:
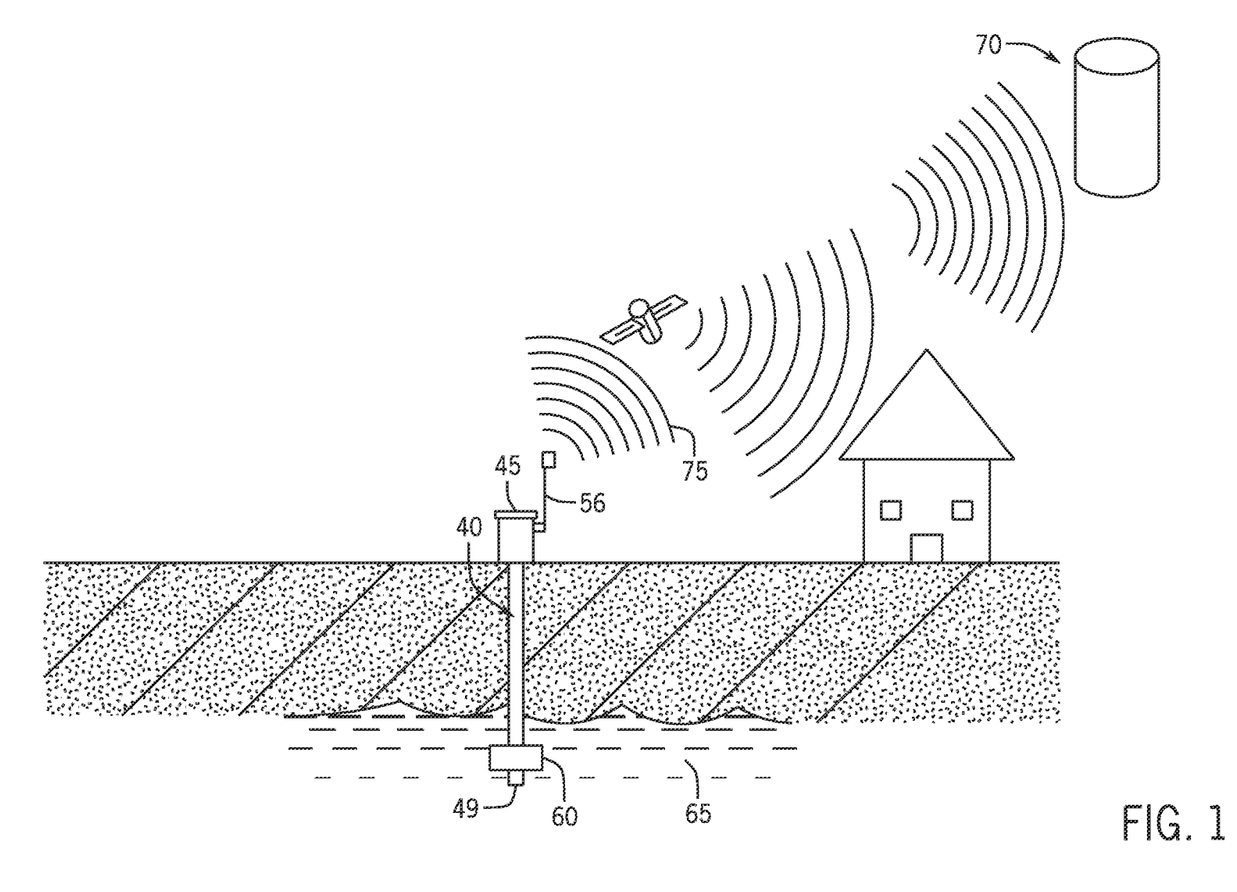
FIG. 1 is a schematic view of one embodiment of a wellhead water quality detector in accordance with the invention.

Referring first to FIG. 1, a water well includes a casing pipe 40 inserted into a borehole in the earth. The borehole is drilled deep enough to encounter groundwater 65. A pump 60 is lowered into the casing pipe 40 and is submerged under groundwater 65. The casing pipe 40 includes an optional screen 49 for screening out sediments through which groundwater 65 seeps. An integrated supply water pipe 50 as shown in FIGS. 2-4, supplies water from the pump 60 to any location, which may include a home.

Figure 2:
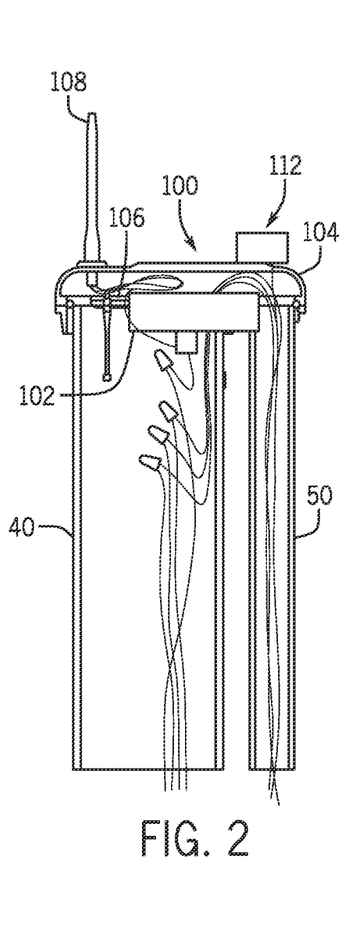
FIG. 2 is a section view of one embodiment of a wellhead water quality detector in accordance with the invention.

Turning to FIG. 2, a wellhead water quality detector 100 for a well in a region where there is a frost line is shown. The wellhead water quality detector 100 has a well air quality sensor 102 inside the well and an ambient air quality sensor 112 outside the well. In the embodiment shown, the standard well cap is removed and a new well cap 104, including the well air quality sensor 102 and other components is installed in its place. Electronics 106 are housed inside the well and under the well cap 104, apart from antenna 108. A data port and battery access port are provided as well. A solar cell and/or other power supplies could also be used instead of, or to supplement the battery.

Figure 3:
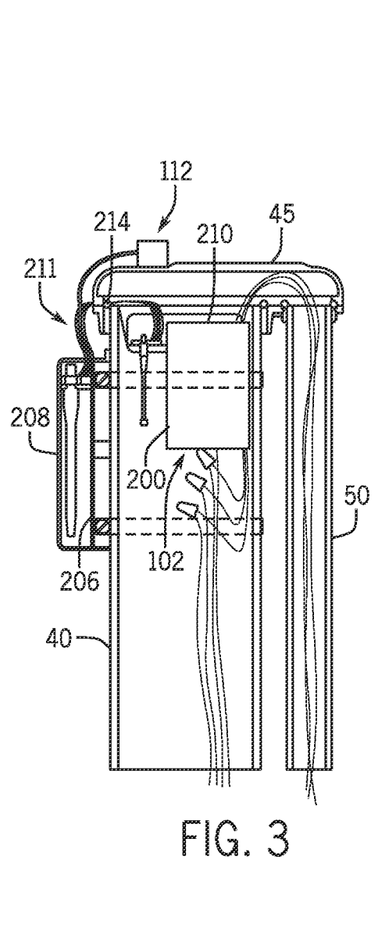
FIG. 3 is a section view of one embodiment of a wellhead water quality detector in accordance with the invention.

Turning now to FIG. 3, a wellhead water quality detector 200 for a well where the existing well cap 45 cannot be replaced is shown. In this embodiment, the wellhead water quality detector 200 is attached to the underside of the existing well cap 45 using any suitable means, e.g. screws, adhesive, etc. External electronics 206 are housed outside of the casing pipe 40 in a rugged housing 208 which can be attached to the pipe. Communication between well air quality sensor 102, ambient air quality sensor 112, and external electronics 206 is made via flat, durable ribbon cable 211 that passes across gaskets 214 without breaking the mechanical, sanitary seals between the casing pipe 40 and the existing well cap 45. Other communication means between the well air quality sensor 102, ambient air quality sensor 112, and the external electronics 206 may also be used, e.g. a wireless communication device.

Figure 4:
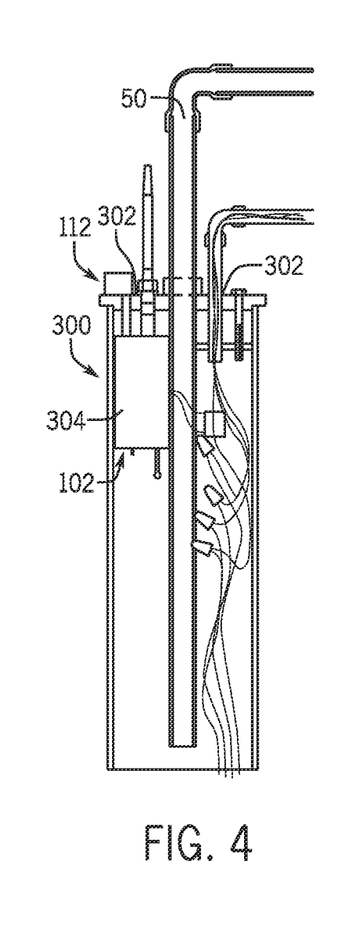
FIG. 4 is a section view of one embodiment of a wellhead water quality detector in accordance with the invention.

Referring to FIG. 4, a wellhead water quality detector 300 for a well in a region where there is no risk of freezing is shown. The wellhead water quality detector 300 utilizes a vent hole 302 common in well caps found in these regions, and will act as a sanitary seal for the hole, while allowing air to be vented. As shown, electronics 304 are housed inside the casing pipe 40, but may also be attached above the well cap outside the well. The well air quality sensor 102 is inside the casing pipe and the ambient air quality sensor 112 is outside the well and both are connected to the electronics 304. The vent hole 302 acts as an access port and conduit for signal and power wires 306 and for mounting hardware.

Furthermore, referring to FIG. 1, the wellhead water quality detector and its related components may alternatively be placed on the outside of the casing pipe 40 or on top of the existing well cap 45. In this configuration, sensors may be attached to the existing well hardware and is configured to be able to gather information through that hardware.

The wellhead water quality detector 100, 200, 300 can be powered using a wide variety of options, from replaceable or rechargeable batteries, to direct line power or low voltage network power, to an optional solar power or other generator.

The embodiments shown in FIGS. 2-4 provide an adaptable wellhead water quality detector that is reliably accurate across a range of well configurations. The embodiments shown in FIGS. 2-4 all include the same components, but vary in how the components are packaged and placed on the well. Each wellhead water quality detector 100, 200, 300 includes a well air quality sensor 102 inside the well, an ambient air quality sensor 112 outside the well, a control circuit, a clock, a memory for logging data, and power and communication circuits.

The embodiments of the wellhead water quality detector 100, 200, 300 shown in FIGS. 2-4 are designed to be installed and forgotten. A photovoltaic cell may be included and may be large enough to provide power for full operation during the day. A battery provides enough power for night time operation, and for extended periods of cloud cover. In the embodiments shown, the battery life is approximately 5 years, by approximating other power consumption variables. Of course, other batteries or power supplies may be used to accommodate wells for any other reason without departing from the invention. An optional solar panel or wand may also be used to extend the height of the solar photovoltaic cells, accounting for deep snow, or bush and plant growth.

The wellhead water quality detector 100, 200, 300 can detect a range of water quality indicators important to the well owner. The well owner may wish to monitor various water quality indicators at the wellhead location for human health and informational knowledge. At a well there are many contaminates which can pose significant threats to humans health, wellness, and property, while other may indicate well water contamination. Such contaminants and indicators include, but are not limited to, volatile organic compounds (VOCs), radon and other radionuclides, natural gasses such as methane, sulfur oxides, nitrous oxides, ammonia and the like.

Volatile organic compounds (VOCs) are harmful to humans and property, and VOCs can be detected in the air column of a well. The US Environmental Protection Agency defines VOCs as "any compound of carbon, excluding carbon monoxide, carbon dioxide, carbonic acid, metallic carbides or carbonates, and ammonium carbonate, which participates in atmospheric photochemical reactions, except those designated by EPA as having negligible photochemical reactivity." VOCs may include, 1,1,1-Trichloroethane, 1,1,2,2-Tetrachloroethane, 1,1,2-Trichloroethane, 1,1-Dichloroethane, 1,1 Dichloroethene, 1,2,3 Trichloropropane, 1,2-Dibromo-3-Chloropropane, 1,2-Dibromoethane, 1,2-Dichloroethane, 1,2-Dichloroethene, 1,2-Dichloropropane, 1,3-Butadiene, 2-Butanone, 2-Hexanone, Acetone, Acrolein, Benzene, Bromodichloromethane, Bromoform & Dibromochloromethane, Bromomethane, Carbon Disulfide, Carbon Tetrachloride, Chlorobenzene, Chloroethane, Chloroform, Chloromethane, Dichlorobenzenes, Dichloropropenes, Ethylbenzene, Formaldehyde, Gasoline Automotive, Hexachlorobutadiene, Hexachloroethane, Hydrazines, Methyl Mercaptan, n-Hexane, Nitrobenzene, Stoddard Solvent, Styrene, Tetrachloroethylene (PERC), Toluene, Trichloroethylene (TCE), Vinyl Chloride, Xylenes, and the like. VOCs can be naturally occurring, however, VOCs are often introduced into groundwater by human activities including industry and agriculture operations, leaking tanks, waste disposal sites, oil drilling, gas drilling, and the like, suggesting that their presence may indicate further groundwater contamination. Once the groundwater is contaminated, it can pose significant health risks to humans and animals. Short-term exposure to VOCs may cause minor health effects such as headaches, nausea, eye, nose, and throat irritation, loss of coordination, and the like. Long-term exposure to VOCs may cause long-term health effects such as cancer, damage to internal organs, allergic skin reactions, emesis, epistaxis, fatigue, and the like. Additionally, elevated levels of VOCs may be flammable and explosive, causing damage to property and threatening human health and safety.

Radon is released into groundwater and quickly volatilized into air by naturally occurring, decaying radioactive uranium and radium. Radon further breaks down into radon progeny which can attach to ambient particulates and can be inhaled or ingested. These radon progeny particles give off high-energy radiation alpha particles which can damage DNA inside human body cells. Radiation from radon in water or air can lead to various health conditions including nausea, skin irritation, cancer, damage to internal organs, and the like. Because of radon's threat to human health, radon is often monitored inside residential homes and in some threatened water supplies. Once radon contamination is detected in the home or in the water, remediation and decontamination is extremely costly. It is beneficial and desirable to detect the presence of radon and other radioactive particles at the wellhead. In this way, the source of radioactive particles, i.e. groundwater, can be identified and can be kept out of the well owner's home. By detecting the particles at the wellhead the well owner can stop the flow of water to the home or install a radon remediation system before residents are exposed. The amount of radon in a well may change over time. Declining groundwater levels and the change in ground water flow due to groundwater pumping and human impacts can increase radon contamination. By locating the wellhead water quality detector on the wellhead, changes in radon concentration may be continuously monitored allowing the well owner to observe and react to changing conditions.

Oil and natural gas are products and bi-products of drilling operations and can contain highly toxic chemicals and can be flammable in high concentrations posing health and safety hazards to humans. Oil and natural gas is often released into the environment through drilling operations, spills at the surface, industrial operations, and waste disposal locations. Once oil or natural gas are detected in water or in the home, remediation costs and decontamination costs can be extremely high. Many homeowners now install gas detectors on the lowest level of the home to detect dangerous, flammable gasses. However, it is beneficial and desirable to detect the presence of natural gas at the wellhead. In this way, oil and natural gas can be kept out of the well owner's home reducing the possibility of exposure to harmful chemicals and reducing the risk of flammable gas accumulation in the home. By detecting natural gas at the wellhead the well owner can stop the flow of water to the home or begin remediation before large concentrations of natural gas develop in the home. Although natural gas can occur naturally in groundwater, the presence of natural gas in a well may be a sign of further contamination associated with nearby oil and gas exploration or drilling practices. Early detection of the presence of natural gas can allow a well owner to proactively assess contamination and begin remediation before there are impacts to human health or property. By continuously monitoring at the well and also monitoring changes between multiple wellheads by linking data through a network, water quality detectors may help identify the source or movement of other contaminants through the aquifer.

Figure 5:
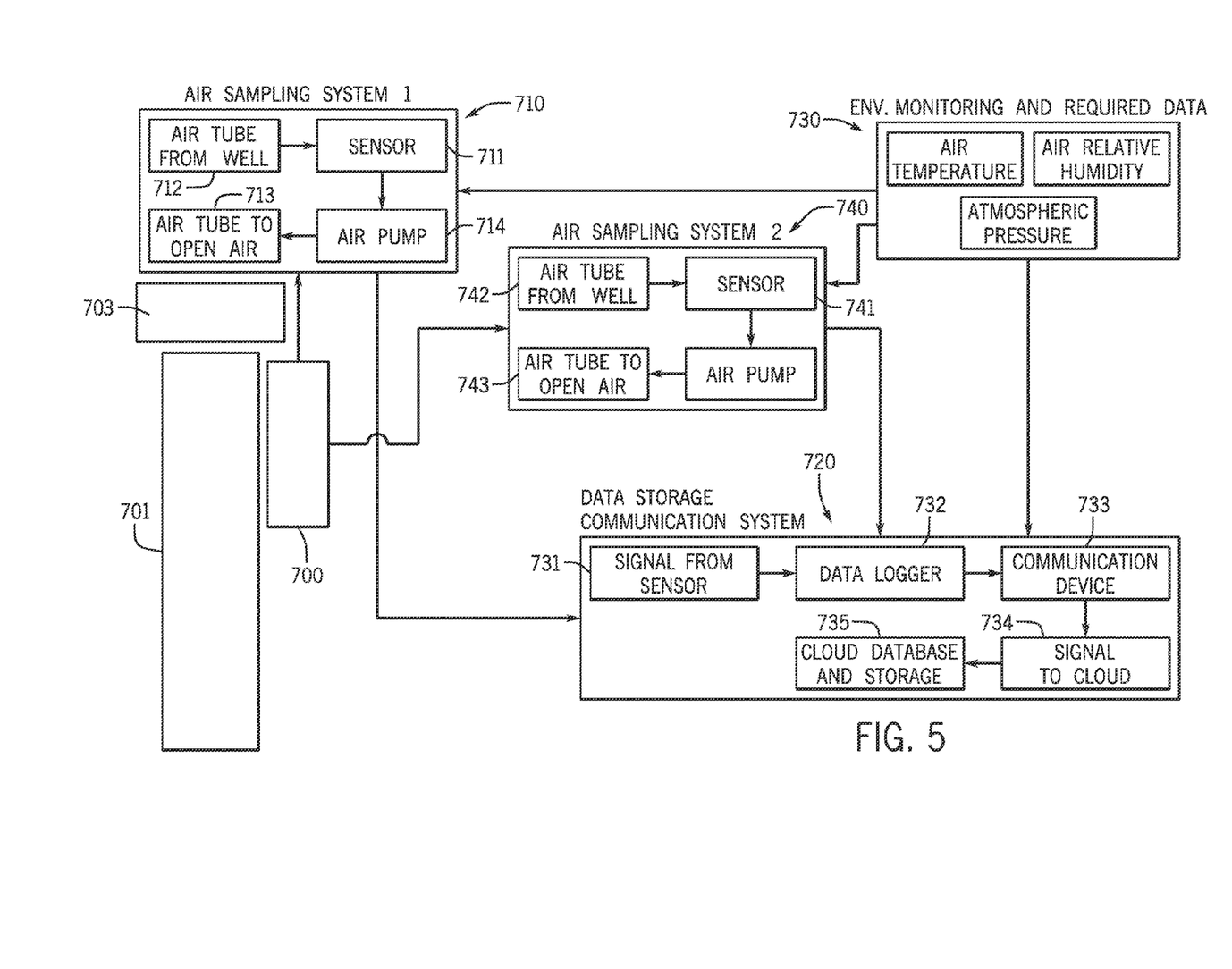
FIG. 5 is a diagram of one embodiment of a wellhead water quality detector in accordance with the invention.

Referring to FIG. 5, a schematic of one embodiment of a wellhead water quality detector 700 in accordance with the invention is shown. Wellhead water quality detector 700 includes an air sampling system 710, a data storage and communication system 720, and an environmental monitoring and data system 730. FIG. 5 shows the wellhead water quality detector 700 on the exterior of the wellhead 703. However, the wellhead water quality detector 700 may be positioned on the interior of the wellhead 703, or a combination of inside and outside the wellhead 703. The air sampling system 710 includes a well air quality sensor 711 for detecting a water quality indicator. The well air quality sensor 711 detects the water quality indicators as the water quality indicators pass by the well air quality sensor 711. The well air quality sensor 711 will detect a specific water quality indicators based on the sensor's detection limits. Depending on the sensor's capabilities, a single sensor could detect one or more water quality indicators. The well air quality sensor 711 may not require any other components attached to it other than a connection to the data and storage and communication system 720.

In the embodiment shown, a second air sampling system 740 is added to the wellhead water quality detector 700. The second air sampling system 740 includes an ambient air quality sensor 741 to measure water quality indicators in the ambient air outside the well 701. Measurable levels of water quality indicators in the ambient air arise from natural occurrences and anthropogenic sources that may or may not be associated with groundwater. In addition, water quality indicator gasses can be advected by wind from long distances resulting in measured changes that are not associated with well water. Using a two sensor system will help accurately identify water quality indicators originating from the well and well water as opposed to those water quality indicators in the ambient air associated with external sources. The well air quality sensor 711 detects values of water quality indicators inside the well 701. The value of well air quality sensor 711 includes water quality indicators in the air from the well water, as well as ambient water quality indicators present in the air near that well 701 that enter the well through wellhead air vents. The ambient air quality sensor 741 detects values of water quality indicators in the ambient air outside the well 701. By comparing the value of the ambient air quality sensor 741 and well air quality sensor 711 in the data storage and communication system 720, with compensation input from an environmental monitoring and data system 730, the well system is able to determine if the air inside the well has a statistically different concentration of the water quality indicator than the air outside the well. If the water quality indicator values inside the well are statistically different than those measured outside the well, the well water is likely contributing water quality indicators to the air inside the well. The water quality indicator values inside the well, from the well air quality sensor 711, and outside the well, from the ambient air quality sensor 741, can be subtracted from each other to determine the value of the water quality indicators in the well water ($WQ_{inside} - WQ_{outside} = WQ_{water}$).

Similarly, the second air sampling system 740 can be added to the wellhead water quality detector 700 to detect a water quality indicator that is different than the first air sampling system 710. The different water quality indicator may be another important water quality indicator to the well owner. It should be known to a person having skill in the art that a plurality of water quality indicator sensors may be added to a wellhead to detect a plurality of water quality indicator values inside the well and the plurality of ambient water quality indicator values outside the well.

In some embodiments, an air tube from the well 712 may be added to direct air to a sensor, such as 711. The air tube from the well 712 allows for a direct channel to the sensor. Depending on the water quality indicator that is being detected the air tube from the well 712 may be positioned further down into the well column below the sensor. The air tube from the well 712 can be positioned at different depths to sample specific water quality indictors or to compensate for stagnant air in the well column. Air tubes may also be added to the ambient air quality sensor 741 to achieve the same results.

In some embodiments, an air tube to open air 713 can be added to the system to direct air away from a sensor, such as 711, after the sensor has detected the water quality indicator. The air tube to open air 713 may be needed if the sensor is positioned on the wellhead where the air leaving the sensor needs to be separated from the air entering the sensor. Air tubes may also be added to the ambient air quality sensor 741 to achieve the same results.

Further still, in some embodiments an air pump 714 can be added to the air sampling system, such as 710, to aid in pushing air to and from a sensor, such as 711. The air pump 714 may be required if the air in the wellhead is sufficiently stagnant making it difficult for the well air quality sensor 711 to accurately detect the water quality indicators. By using the air pump 714, the correct quantity and rate of air researches the sensor for detection. An air pump may also be added to the ambient air quality sensor 741 to achieve the same results.

The wellhead water quality detector 700 also includes an environmental monitoring and data system 730. The environmental monitoring and data system 730 accounts for external factors affecting the detection capabilities of the air sampling system 710. External factors that may be included in the environmental monitoring and data system 730 are air temperature, air relative humidity, and atmospheric pressure. The external factors are used by the air sampling system 710 and a data storage and communication system 720 to improve accuracy of measurements through calculations made using sensor output. It should be understood by a person skilled in the art that the environmental monitoring and data system 730 may include any external factor which affects the wellhead water quality detector 700 or the detection of a specific water quality indicator in the air.

The wellhead water quality detector 700 also includes a data storage and communication system 720. The data storage and communication system 720 operates by receiving a signal from sensor 731. The signal from sensor 731 is logged by the data logger 732. The data leaves the data logger 732 via a communication device 733 by a signal to a network or database, also referred to as "the cloud" 734 which allows the data to be stored and processed for analysis, interpretation, alerts, and visualization in cloud databases and storage 735.

The data storage and communication system 720 transmits a signal containing water quality indicator data to a globally accessible network. Referring to FIG. 1, a globally-accessible network 70 in the form of a satellite, the network may also be a cellular tower, the internet, a WiFi connection or any suitable network. Transmission device 56 within wellhead water quality detector transmits water quality indicator data to a wireless network 75. The water quality indicator data transmitted to the network may include all water quality data or the important information created by the communication circuit. The wireless network 75 may then relay the computed target water quality information to a globally-accessible network 70 which may include the internet, the World Wide Web, or any other known globally accessible network. A handheld device which may include a smart phone, a tablet computer, a pager, or any computer that has access to the globally-accessible network 70 may then access an application or website that displays the water quality data in any form, including a graph. Alternatively, a computer may be used to download the water quality data from the water well. Wellhead water quality detector 100 may be programmed to periodically transmit a data set which may include the target water quality information to the wireless network.

Alternatively, the wellhead water quality detector 100 can transmit water quality indicator data by way of a pre-existing wireless network. The pre-existing wireless network may be available from other devices attached to the wellhead or other wellhead detectors, such as the device disclosed in U.S. Pat. Appl. Publ. No. 2014/0009302 titled WELLHEAD WATER LEVEL SENSOR, the disclosure of which is incorporated herein for all purposes. By utilizing other wireless networks and their related electrical components, such as circuitry, communication devices, motherboards, and the like, the wellhead water quality detector can be easily added to other devices at the wellhead. Also, by utilizing other devices at the well, the wellhead water quality detector's cost, material requirements, installation time, and maintenance time is decreased.

Referring to FIG. 2, to enable semi-continuous monitoring of a water well, it is necessary to position the well air quality sensor 102 in such a way that the sensors can measure water quality indicators inside the well while not needing to open the well or expose the inside of the well to open air, water, or other contamination and to leave them there, to operate over months and years. Additionally, its work must be done and information collected and accessed or transmitted at the surface without special tools or connections. The embodiments shown in FIGS. 2-4 are designed to either replace an existing cap or utilize existing vents and access points without leaking or altering normal operation of the well.

The sensors, such as 102 shown in FIG. 2, detect a water quality indicator. The sensors may utilize various sensing technologies to detect the target water quality indicator. The sensing technology can involve metal oxide semiconductors, conducting and nonconducting polymers, carbon nanotubes, absorption spectrometry and other optic and infra-red gas sensing methods, alpha particle and radiation detectors, portable gas chromatographs, calorimetric gas sensors, and the like. In some embodiments, more than one gas sensing technology may be used by a well head water quality detector.

The air to be detected by the sensors can be air from inside the well, outside the well, or surrounding the well depending on the requirements of the wellhead water quality detector, such as 100 shown in FIG. 2 or the specific indicator to be detected. The sensor may detect the water quality indicator without air flow across the sensor. A common language name for these types of sensors is a "sniffer," such as residential home smoke detectors or carbon monoxide detectors.

However, some sensors require the flow of air across, through, around, next to, adjacent, or the like, for the sensor to detect the water quality indicator. For sensors requiring a flow of air to detect the water quality indicator, the flow of air can be provided by the flow of air in and out of the well during water pump operation and well water drawdown and recovery. In this situation air flows in the following way. When the well is in a static state, no flow of air occurs between the inside and outside of the well. When water is pumped out of the well by a pump, the well water level decreases. During the pumping activity, a flow of air into the well occurs by way of relief valves or holes near the top of the well and wellhead to fill the space left void by the water being pumped out. As the well water level in the pump is recharged by the surrounding groundwater, the air in the well is pushed out of the well through relief valves or holes near the top of the well. When this flow of air occurs, the volume of air forced into and out of the well due to pumping drawdown and groundwater recovery can be estimated based on the known diameter of the well and the change in water level in the well. Placing the water quality detector in or near this flow of air provides the required flow of air to the sensor. In some cases air flow can be produced through natural processes such as if there is a rapid external atmospheric pressure change or if there is an unstable air column in the well which can be caused by groundwater which has a higher temperature than the air temperature in the well.

Such situations are caused by weather patterns or are seasonal and regional in nature and, therefore, cannot be relied on in all instances to provide a flow of air for the sensor. The water level of the of the well can be calculated by dividing the volume of air passing the sensor by the cross-sectional area of the well (Volume$_{air\ passing\ sensor}$/((pi)* (radius$_{well\ pipe}$)^2)=Distance$_{to\ water\ level}$).

Figure 6A:
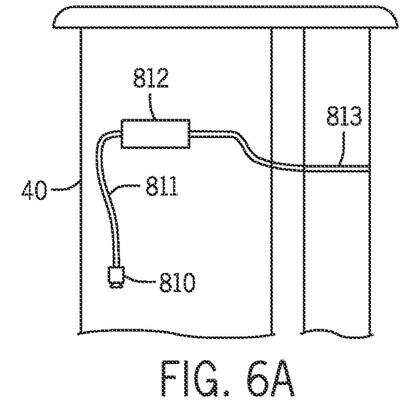
FIG. 6A-6E are section views of embodiments of a wellhead water quality detector including an air pump in accordance with the invention.
Figure 6B:
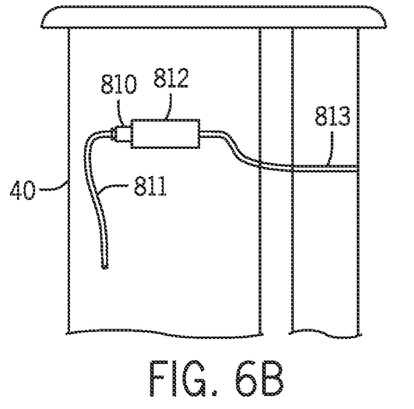
Figure 6C:
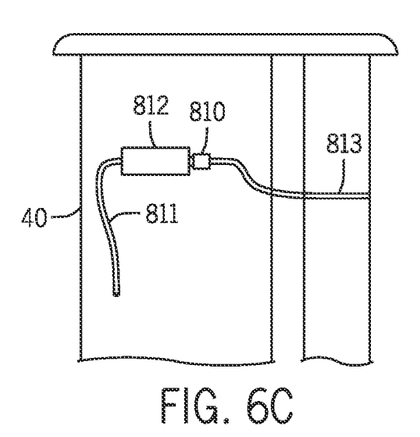
Figure 6D:
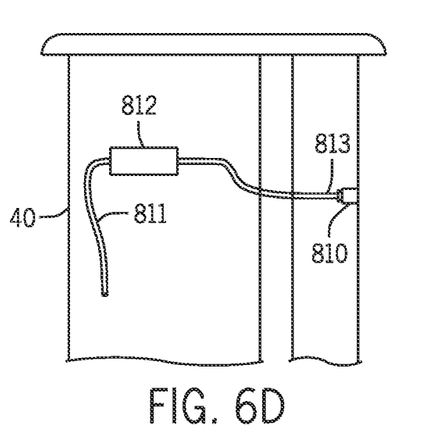
Figure 6E:
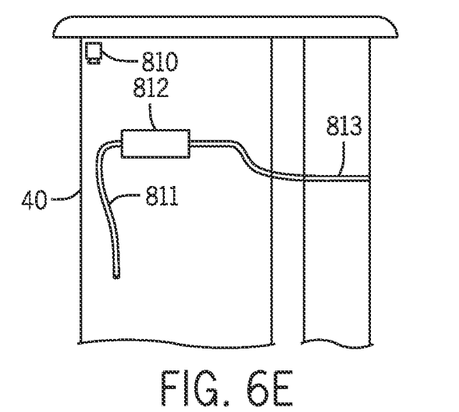

Alternatively, referring to FIG. 6A-6E, a mechanical or electrical air pump 810 can be provided to increase the flow of air to the wellhead water quality detector. The air pump 810 may be necessary when there is inadequate air flow in and out of the casing pipe 40 to allow the sensor to function properly. Based on the water quality indicator to be detected, air composition, location of wellhead, location of the wellhead water quality detector, space constraints of the wellhead water quality detector in the wellhead, and other like reasons, the air pump 810 can be located in various positions and orientations inside, outside, and around the wellhead. Referring to FIG. 6A, the air pump 810 can be connected at the entrance of the entry air tube 811. Referring to FIG. 6B, the air pump 810 can be connected between the entry air tube 811 and the sensor 812. Referring to FIG. 6C, the air pump 810 can be connected between the sensor 812 and the exit air tube 813. Referring to FIG. 6D the air pump 810 can be connected at the exit of the exit air tube 813. Referring to FIG. 6E, the air pump 810 can be located in a position not connected to the entry air tube 811, sensor 812, and exit air tube 813. FIG. 6A-6E show entry and exit air tubes, but these air tubes may be excluded in some embodiments of the invention.

Figure 7:
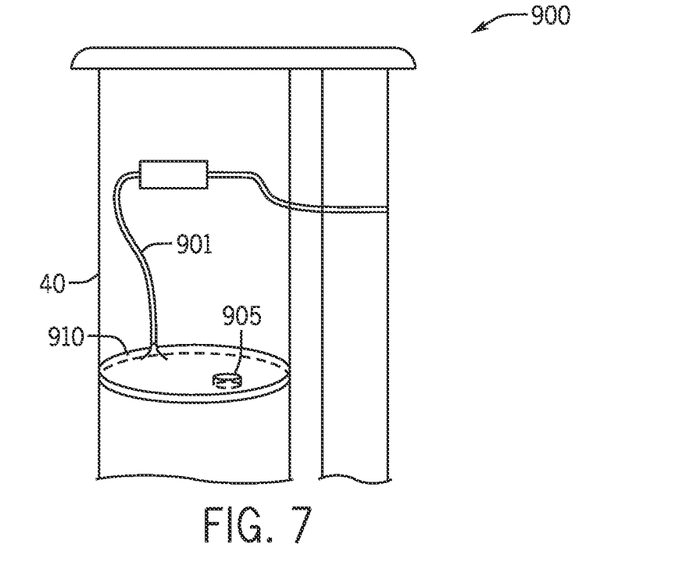
FIG. 7 is a section view of one embodiment of a wellhead water quality detector in accordance with the invention.
Figure 8:
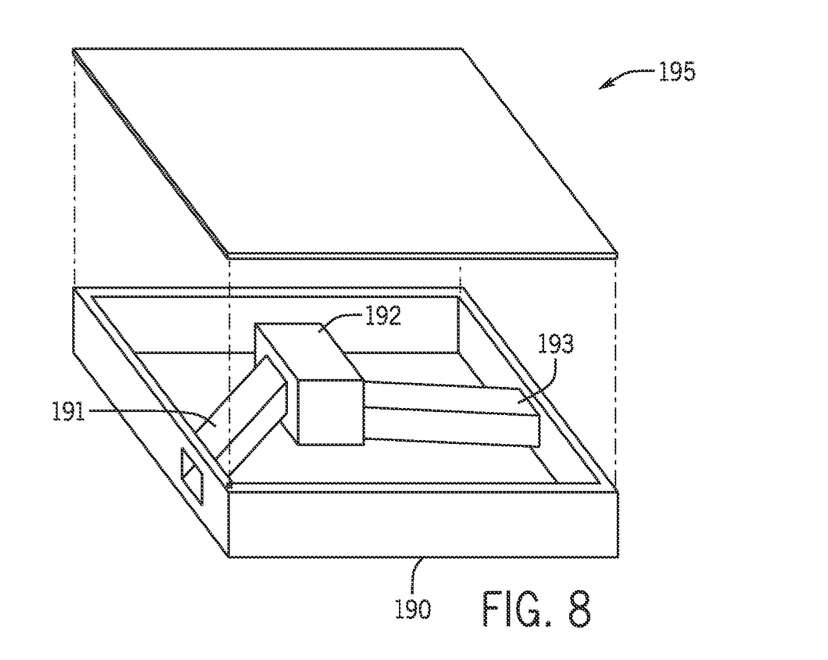
FIG. 8 is a schematic view of one embodiment of a wellhead water quality detector in accordance with the invention.

In addition, referring to FIG. 7, if flow of air due to water pumping, air pumping, or other natural processes is inadequate or impossible for an accurate sensor reading, an air funnel 910 may be added to the wellhead water quality detector 900 to concentrate the airflow to the sensor 902. The air funnel 910 fits tightly to the inside of the casing pipe 40 so that no air passes around the air funnel 910. The air must pass through the opening in the air funnel 910. Air flow is increased through the air funnel 910 and when the sensor 902 is connected to the air passage 901 of the air funnel 910 the air flow to the sensor is increased. When the flow of air is back into the well, the air flows in the reverse direction past the sensor 902 through the hole in the funnel. Alternately, the flow of air back into the well may pass by way of release one-way valve 905 in the air funnel 910.

Referring to FIG. 7, if an air tube to open air 713 and an air tube from the well 712 are required, the air tubes can be constructed out of any material appropriate for placement near a well. The selection of the material for the air tubes should take into consideration factors such as humidity levels in and near the well, pest management, temperature, material availability, material cost, corrosion, ultraviolet light exposure, and like factors. Additionally, the material selected for the air tubes need not necessarily be the same material. Materials utilized can include plastic, plastic-metal composite, metal, or other non-gas-permeable material. Furthermore, requirements of the sensor, such as 711 in FIG. 7, may require the air tubes to be made of material which will not contaminate or alter the air reaching the sensor which may affect the water quality indicator detection. Even further still, the air tubes need not be constructed out of any physical material. The air passages may be void spaces where the sensor is positioned or orientated to take advantage of void spaces.

The entrances to the air tubes can be located in various positions around the wellhead. The air passages may need to be located in different locations in and around the wellhead based on the water quality indicator being detected by the sensor. Temperature, temperature gradients, humidity, atmospheric pressure, ultraviolet light, and the like, may affect the target water quality indicator as the air moves toward the sensor, and thus, the air tubes may be located inside or outside the well to minimize these alternations on the target source detection.

Referring to FIG. 10, a housing 190 may be used to organize the entry air tube 191, sensor 192, and exit air tube 193 into one unit. The housing 190 protects the other components of the wellhead water quality detector 100 such as the entry air tube 191, sensor 192, and exit air tube 193 from damage. The housing 190 may be constructed out of any material appropriate for placement near a well. The selection of the material for the housing 190 will require consideration of humidity levels in and near the well, pest management, material availability, material cost, corrosion and like factors. The housing 190 can be waterproof, tamper-proof, vermin-proof, and durable enough to withstand small contact with branches, weeds, a passing lawn mower, or the like. The material selected for the entry air tube 191 and exit air tube 193 need not be the same material as the housing 190. Materials utilized for the housing 190 can include plastic, plastic-metal composite, metal, wood, fabric or cloth. In a similar embodiment, the housing 190 may integrate the entry air tube 191 and the exit air tube into the material of the housing 190. The housing 190 may also protect the second sensor. Alternately, a second housing can be provided to protect the second sensor.

Although the invention has been herein described in what is perceived to be the most practical and preferred embodiments, it is to be understood that the invention is not intended to be limited to the specific embodiments set forth above. Rather, it is recognized that modifications may be made by one of skill in the art of the invention without departing from the spirit or intent of the invention and, therefore, the invention is to be taken as including all reasonable equivalents to the subject matter of the appended claims and the description of the invention herein.

What is claimed is:

1. A wellhead water quality detector for use in a water well having a casing pipe inserted deep enough into the ground to encounter groundwater and a well cap, the well head water quality detector device comprising:
   a well air quality sensor attached inside the well below the well cap and above the groundwater;
   the well air quality sensor including at least one environmental sensor;
   an ambient air quality sensor attached outside the well and including at least one environmental sensor;
   the well air quality sensor and the ambient air quality sensor communicatively attached to electronics; and
   the electronics including a control circuit, a clock, memory for storing data and a communication circuit for transferring data obtained from the sensors to a globally accessible network.

2. The wellhead water quality detector of claim 1, wherein the water quality detector is an integral part of the well cap.

3. The wellhead water quality detector of claim 1, wherein the water quality detector is integrated into a new well cap which replaces the existing well cap.

4. The wellhead water quality detector of claim 1, wherein the water quality detector is attached to the well cap by adhesive.

5. The wellhead water quality detector of claim 1, wherein the water quality detector is attached to the well cap by at least one screw.

6. The wellhead water quality detector of claim 1, wherein the water quality detector is mounted to the exterior of the well.

7. The wellhead water quality detector of claim 1, wherein the well air quality and ambient air quality sensors detect volatile organic compounds.

8. The wellhead water quality detector of claim 1, wherein the well air quality and ambient air quality sensors detect radon.

9. The wellhead water quality detector of claim 1, further including at least one air tube to direct air toward the well air quality sensor.

10. The wellhead water quality detector of claim 1, further including an air pump to generate airflow across the well air quality sensor.

11. The wellhead water quality detector of claim 1, further including an air funnel to direct air toward the well air quality sensor.

12. The wellhead water quality detector of claim 1, wherein the water quality detector communicates with a globally accessible network.

13. The wellhead water quality detector of claim 1, wherein the water quality detector communicates with a globally accessible network.

14. The wellhead water quality detector of claim 1, wherein the water quality detector includes a housing.

15. The wellhead water quality detector of claim 1, wherein the water quality detector includes a battery.

16. The wellhead water quality detector of claim 1, wherein the water quality detector includes a photovoltaic cell.

17. The wellhead water quality detector of claim 1, further including a wireless communication device.

18. The wellhead water quality detector of claim 1, wherein the well air quality sensor does not contact the groundwater.

19. A method of determining water quality of well water at a well having a casing pipe inserted deep enough into the ground to encounter groundwater and a well cap, the method comprising the steps of:
   placing a well air quality sensor in the well above the groundwater;
   placing an ambient air quality sensor outside the well;
   connecting the well air quality sensor to a control circuit;
   connecting the ambient air quality sensor to the control circuit;
   recording data from the well air quality sensor and ambient air quality sensor;
   transferring the data to a memory;
   communicating the data from the memory to a globally accessible network; and
   comparing the data obtained from the well air quality sensor to the data obtained from the ambient air quality sensor.

20. The method of claim 19 further including the step of adjusting the data based on data received from remote environmental monitoring sensors.

21. The method of claim 19 further including the step of tracking water quality indicator data at a plurality of well locations by network system.

* * * * *